United States Patent
Hatti et al.

(10) Patent No.: US 10,918,749 B2
(45) Date of Patent: Feb. 16, 2021

(54) AIRCRAFT CABIN DISINFECTION SYSTEM

(71) Applicant: Airbus SAS, Bristol (GB)

(72) Inventors: Prakash Hatti, Bristol (GB);
Arumugam Thinket Selvan, Bristol (GB)

(73) Assignee: Airbus SAS, Bristol (GB)

(*) Notice: Subject to any disclaimer, the term of this patent is extended or adjusted under 35 U.S.C. 154(b) by 169 days.

(21) Appl. No.: 16/037,496

(22) Filed: Jul. 17, 2018

(65) Prior Publication Data
US 2019/0030195 A1 Jan. 31, 2019

(30) Foreign Application Priority Data
Jul. 28, 2017 (IN) .............................. 201741026979

(51) Int. Cl.
*A61L 2/10* (2006.01)
*B64F 5/30* (2017.01)
*A61L 2/24* (2006.01)

(52) U.S. Cl.
CPC ....... *A61L 2/10* (2013.01); *A61L 2/24* (2013.01); *B64F 5/30* (2017.01); *A61L 2202/14* (2013.01); *A61L 2202/16* (2013.01); *A61L 2202/25* (2013.01)

(58) Field of Classification Search
CPC .......... A61L 2/10; A61L 2/24; A61L 2202/14; A61L 2202/16; A61L 2202/25; B64F 5/30
See application file for complete search history.

(56) References Cited

U.S. PATENT DOCUMENTS

| | | | |
|---|---|---|---|
| 8,907,304 B2 | 12/2014 | Kreitenberg | |
| 9,517,280 B2* | 12/2016 | Lynn | .......................... A61L 2/10 |
| 2007/0053188 A1* | 3/2007 | New | ...................... B64D 13/00 362/276 |
| 2014/0059796 A1 | 3/2014 | Boodaghians et al. | |
| 2015/0317797 A1 | 11/2015 | Lu et al. | |
| 2016/0136314 A1* | 5/2016 | Kreitenberg | .............. B64F 5/30 422/24 |

FOREIGN PATENT DOCUMENTS

| | | |
|---|---|---|
| GB | 2 527 964 | 1/2016 |
| JP | 2016-066308 | 4/2016 |
| KR | 10-2015-0017544 | 2/2015 |

OTHER PUBLICATIONS

Combined Search and Examination Report for GB 1715458.4, dated Mar. 14, 2018, 6 pages.

* cited by examiner

*Primary Examiner* — Timothy C Cleveland
(74) *Attorney, Agent, or Firm* — Nixon & Vanderhye P.C.

(57) ABSTRACT

A cabin disinfection system for an aircraft, including: a sensing means (3, 11, 13) to sense the presence of personnel in one or more zones (16-19, 23-26, 28, 29, 30, 32), a predictive sensing means (3, 11, 13, 33) to sense the direction of motion of a person (31) and to predict whether that person will occupy a zone to be disinfected (18) during planned disinfection, one or more UVC radiation sources (4, 9) to disinfect the cabin, and a controller (33) to control operation of the UVC radiation sources (4, 9) dependent on sensing of personnel in that zone and the predictive sensing means (3, 11, 13, 33) predicting that a person (31) will occupy the zone (18) during the planned disinfection period.

19 Claims, 4 Drawing Sheets

AIRCRAFT CABIN DISINFECTION SYSTEM

RELATED APPLICATION

This application claims priority to Indian patent application 2017/41026979, filed 28 Jul. 2017, the entirety of which is incorporated by reference.

FIELD OF THE INVENTION

The present invention relates to a system for disinfection of an aircraft cabin and more particularly to such a system which will disinfect a portion of the cabin while people are present in the cabin in the aircraft.

BACKGROUND

It is known to provide an aircraft cabin ultra-violet C light (UVC) disinfection system for a passenger cabin in a commercial aircraft. The system uses motion sensors to detect the presence of personnel in the affected area of the cabin and only disinfect when no personnel are detected. These known systems are restricted in their operation and will only operate to disinfect a cabin when no personnel are present in the affected area of the cabin. There is a need to provide a cabin disinfection system which mitigates these restrictions.

SUMMARY OF THE INVENTION

The invention may be embodied as a cabin disinfection system for the cabin in an aircraft. The system may include: (i) a sensor configured to sense the presence of personnel in one or more zones of the cabin to be disinfected, (ii) a predictive sensing module configured to sense the direction of motion of a person in the one or more zones of the cabin to be disinfected and predict whether that person will occupy a zone selected to be disinfected during a planned disinfection period, (iii) one or more UVC radiation sources adapted to disinfect the cabin in the selected zone, and (iv) a controller configured to actuate the one or more UVC radiation to disinfect a selected zone of the cabin depending on whether the sensor has sensed personnel in the selected zone and whether the predictive sensing module has predicts that a person will occupy the selected zone during the planned disinfection period.

The controller may be one or more computers having software to analyze incoming data from sensors, such as video cameras, to make decisions based upon that data and to issue instructions accordingly to the UVC radiation sources whereby to disinfect one or more zones of the aircraft cabin.

The system may include intensity measuring sensor to measure the intensity of UVC radiation in the selected zone.

The controller may include an adjustment module configured to adjust the measured intensity of the UVC radiation to a predefined or preferred level as required. Thus, if the intensity of radiation is measured to be too high, the intensity may be adjusted by altering the electrical voltage applied to the UVC radiation source or lamp.

Alternatively or in addition, a radiation beam focusing device, such as a lens, may be used to converge or diverge the UVC radiation beam. The radiation beam focusing device will have the effect, respectively, of increasing or decreasing the beam intensity.

Further, a gimbal may be used to sweep the beam across an area (zone) of the cabin selected for disinfection. Radiation intensity of the UVC radiation beam at the surfaces of the cabin may be increased or decreased, respectively, by slowing down or speeding up the sweep speed.

By means of the above adjustment means, UVC intensity may always be kept below allowed UVC human exposure limits. Such a safety feature will enhance passenger safety if, for example, UVC disinfection is erroneously activated with people present in the disinfection zone.

The system may include zone counting means to count the number of persons present in the selected zone.

The system may include cabin counting means to count the number of persons present in the cabin.

One or more zones in the aircraft cabin may be selected from seating areas, subsets of seating areas, galleys, lavatories, social areas such as bars, staircases and crew rest areas. Also, the cabin may include the cockpit.

The system may include one or more visible light sources controllable by the controller to illuminate the said one or more zones of the cabin. Hence, the controller may be operable to control the one or more visible light sources and the one or more UVC radiation sources to illuminate the one or more zones with visible light, with UVC radiation, with a combination of visible light and UVC radiation or with no visible light and no UVC radiation.

The predictive sensing module may be operable to predict whether a person will occupy a said zone to be disinfected during a planned disinfection period by sensing a position of that person and a speed of movement of that person toward the said zone to be disinfected. Similarly, the predictive sensing module may be operable to predict whether a person will occupy a said zone to be disinfected during a planned disinfection period by sensing a position of that person and a speed and direction of movement of that person out of the zone to be disinfected.

The sensor may be operable to sense the presence of personnel in one or more zones of the cabin to be disinfected at least in part by detecting seat occupancy.

The sensor may include a video camera operatively linked to video analytics software to sense the presence of persons.

The video camera may be an IR video camera adapted to detect a person's body temperature whereby to detect the presence of a person or to identify raised body temperature associated with possible illness.

The controller may be operable to control the one or more UVC radiation sources whereby to ensure that a predetermined dose of UVC radiation is administered to a given cabin zone. The controller may be ensured that enough UC radiation is delivered to provide effective disinfection, according to known disinfection parameters. The controller may also avoid excessive unsafe dosing in areas of the cabin which are near people.

The controller may be configured to control disinfection of the one or more cabin zones in dependence upon a flight mode of the aircraft. The flight modes may include: parked and unoccupied; taxiing; in flight; in flight and X minutes from take-off; in flight and X minutes from landing, where "X" represents a desired number of minutes designed into the system. By being operable in different flight modes, the system may therefore operate with much more flexibility than known disinfection systems.

The system may include an array of multifunction UVC units distributed throughout the aircraft. Each of the multifunction UVC units may include a source of UVC radiation, a sensor, a predictive sensing module, and a controller, with at least two multifunction UVC units being operatively linked together.

Movement of personnel may be sensed or predictively sensed using an array of IR video cameras in conjunction with standard cabin video cameras and video analytics software to analyze the video images.

The sensor may include an array of sensors comprised in the group passive infra-red and ultrasonic and such sensors may be distributed throughout the cabin and used to sense movement of personnel. Such sensors may also be used to activate one or more of the cameras.

The invention may be embodied as an aircraft having a cabin disinfection system as described above.

The invention may also be embodied as a method of disinfecting a zone in an aircraft cabin, the method including the steps of: (i) sensing whether any persons are present in the zone to be disinfected, (ii) sensing whether any persons are moving relative to the zone to be disinfected and/or are predicted to occupy the zone during planned disinfection, and (iii) if no such persons are sensed or predicted to occupy the zone, controlling a UVC radiation source to carry out disinfection of the zone.

BRIEF DESCRIPTION OF THE DRAWINGS

The present invention will now be described, by way of example only, with reference to the following drawings in which:—

DETAILED DESCRIPTION OF THE INVENTION

Figure 1:
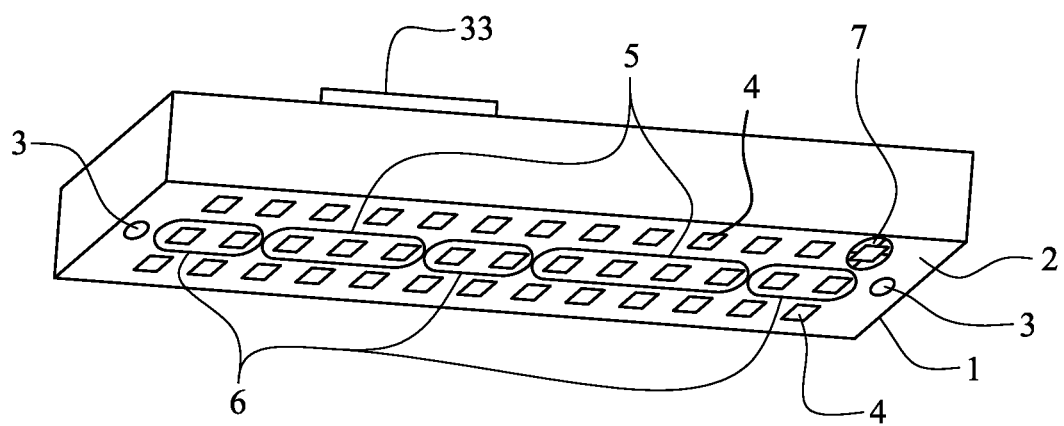
FIG. 1 is a perspective view of a multifunction UVC unit according to the invention.

FIG. 1 shows a multifunction ultra-violet light (UVC) unit 9 suitable for the cabin, such as a passenger cabin, of a commercial aircraft. UVC refers to Ultraviolet C light having wavelengths in 100-280 nm, which is useful to disinfect surfaces exposed to the UVC light. The UVC unit 9 comprises a rectangular body 1 having a mounting plate 2. Set into the mounting plate 2 are two motion and occupancy sensors 3 in the form of IR video cameras, two rows of UVC lamps 4, seven light intensity measuring sensors 5 and six visible light lamps 6. The UVC lamps 4 are mounted on gimbals 7. A controller 33 for the UVC unit is also shown on the rear of the body 1. Individual controllers 33 for each UVC unit are linked into a central controller (see FIG. 5) for the whole disinfection system.

Figure 2:
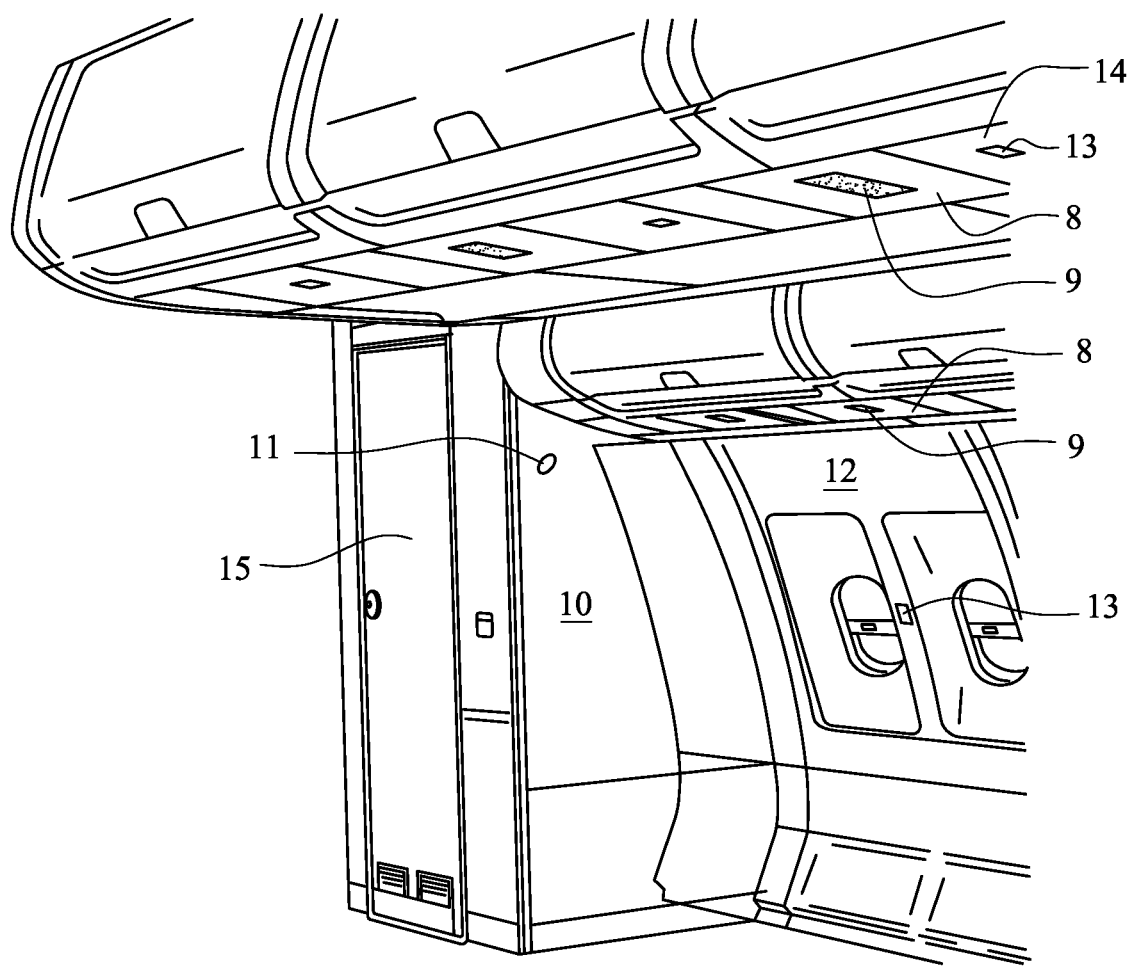
FIG. 2 is a perspective view of an aircraft cabin showing positioning of various aspects of the invention within the cabin.

FIG. 2 shows the positioning of multifunction UVC units 9, video cameras 11 and sensors 13 in a seating section of an aircraft cabin (seats not separately shown). Mounted in passenger service units 8 are the multifunction UVC units 9. The UVC units 9 may be mounted at convenient locations in the cabin, such as above and in the backs of seats. The UVC units apply ultra-violet (UV) light to the surfaces of the seats and other exposed surfaces in the cabin. The UV light disinfects these surfaces.

Mounted on bulkhead and/or partition wall(s) 10 in the cabin is a video camera(s) 11 which provides a field of view of the entire cabin or at least a substantial portion of the cabin. Additional video cameras may be mounted in the aircraft to provide a complete view of the cabin and all possible locations of personnel in the cabin. Mounted on cabin wall 12 at various locations are movement sensors 13 which may be of the passive infra-red or ultrasound type. Similar movement sensors 13 may be mounted at various locations in the cabin ceiling 14. The movement sensors 13 are distributed in the cabin to sense the movement of any personnel in the cabin. Installed in lavatory 15 is a further UVC unit (not shown). Other occupancy or movement sensors may be mounted in or at the entrance of a lavatory to detect the presence of a person in the lavatory. The UVC units and sensors may also be installed in other portions of the interior of the aircraft and its cabin, such as galleys, crew rest areas, stairways, bars or lounge areas and the cockpit.

The invention may be embodied as a cabin disinfection system for an aircraft, including: a sensing unit (3, 11, 13) to sense the presence of personnel in one or more zones (16 to 19, 23 to 26, 28, 29, 30, 32), a predictive sensing unit (3, 11, 13, 33) to sense the direction of motion of a person (31) and to predict whether that person will occupy a zone to be disinfected (18) during planned disinfection, one or more UVC radiation sources (4, 9) to disinfect the cabin, and a controller (33) to control operation of the UVC radiation sources (4, 9) dependent on sensing of personnel in that zone and the predictive sensing means (3, 11, 13, 33) predicting that a person (31) will occupy the zone (18) during the planned disinfection period.

Figure 3:
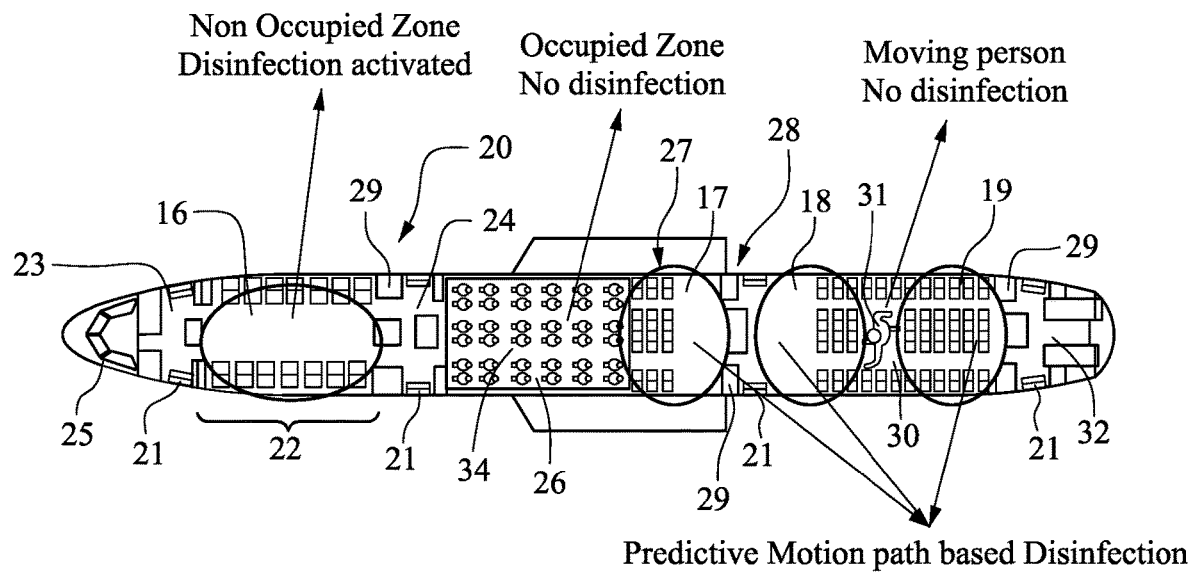
FIG. 3 is a schematic view from above of an aircraft interior, showing disinfection of different zones on the aircraft.
Figure 4:
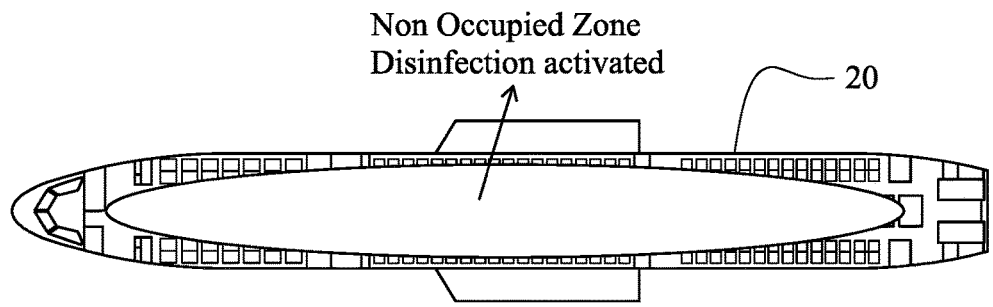
FIG. 4 is a further view of the aircraft interior of FIG. 3, showing disinfection of substantially the whole interior of the aircraft.

FIGS. 3 and 4 show an aircraft interior, from above, illustrating disinfection of different areas of the interior of the aircraft 20. The interior may be the passenger cabin in which rows of passenger seats are separated in sections, such as by classes of service and by monuments, such as lavatories and galleys. FIG. 3 illustrates disinfection of four separate ovoid zones 16, 17, 18, 19 in the cabin, such as zones having an egg-shaped or oval area within the cabin. FIG. 4 shows disinfection taking place in a single ovoid zone that extends the entire passenger cabin of the aircraft 20. In the case shown in FIG. 4, the cabin of the aircraft 20 is completely unoccupied and the whole cabin may be safely disinfected at the same time. The fact that the aircraft is unoccupied may be ascertained based on data obtained from the motion sensors 13 distributed throughout the cabin, standard video cameras 11, and UVC units 9 indicating that no persons are detected to be present.

The sensors 13, video cameras 11 and motion and occupancy sensors 3 (one or more of which form a zone counting module) contained in UVC units 9 in the region of entrances 21 of the aircraft 20 may be used to count the number of people boarding and disembarking from the aircraft. When the number counted to be on board the aircraft is zero, disinfection may be carried out throughout the entire interior of the aircraft. A personal inspection of the aircraft may also be relied upon, to permit disinfection.

Referring to cabin zone 16, as shown in FIG. 3, this zone has been ascertained to be completely unoccupied and is therefore safe for disinfection to be carried out. The detection that zone 16 is unoccupied and treatment should proceed using the same logic used to determine that the entire cabin of the aircraft 20 shown in FIG. 4 was unoccupied and ready for treatment. In particular, occupancy sensors 3 positioned in the ceilings above the aircraft seats may indicate that all seats are unoccupied. Occupancy sensors 3, such as motion sensors, may comprise miniature IR video cameras used to detect movement and to detect an occupant's heat. A lack of movement and a lack of detected heat will indicate that no one is in the seats within the sensor range of each of the occupancy sensors 3.

Whereas a count of persons entering and leaving the aircraft through the entrances 21 will ensure an accurate tally of persons on the aircraft, for the case illustrated in FIG. 4, for zone 16, further information as to head count will be required. This is because galleys 23, 24 and cockpit 25 are adjacent seating area 22 and information as to the number of people, if any, in these adjacent cockpit and galley areas 23, 24, 25 will be required. Unless galleys 23, 24 and cockpit 25 are unoccupied it may not be safe to disinfect seating area 22 as a person or persons could easily stray into the seating area 22 while it is being disinfected (see later in respect of zones 18, 19, however, for further discussion on areas adjacent to disinfection zones).

Thus, for zone 16, it is necessary to count not only persons entering the aircraft through each entrance 21 but it is also necessary to count those people passing through galley 24, in either direction. Galleys 23, 24 may be fitted with sensors 3, 13 and possibly standard video cameras 11. Sensors 3 may be fitted to UVC units as in the passenger compartment.

In regard to occupied zone 26, sensors 3 mounted in passenger service units 8 above the seats in zone 26 will all register seat occupancy and no disinfection will be possible.

Ovoid zones 17, 18 and 19 are being disinfected but, it will be observed in the cases of zones 17 and 19, with an increasing intensity from left to right. In the case of zone 18, the increase in intensity is from right to left. In each case the decrease in intensity occurs as the disinfection zone approaches one or more persons.

Because disinfection by UVC radiation is carried out by the individual UVC units over each seat, it is possible to vary the UV intensity by activating only certain units or by modulating power applied to the units. UVC measuring sensors 5 are used to measure the intensity of UV radiation output from the UVC units. The measured intensity is then relayed to one or more controllers 33 (see FIGS. 1 and 5) which then adjust the UVC radiation level of one or each UVC unit as required to achieve the desired level of UVC radiation at any particular position in the aircraft. One or more controllers 33 are here located within one or more UVC units but could be located anywhere in the aircraft and be stand-alone units or could be part of a larger system, such as an in-flight communication system or an air conditioning system.

Thus, where it is desired to disinfect an area adjacent to an occupied zone, the intensity of UVC radiation may conveniently be reduced to zero at a position nearest to the person or persons adjacent the disinfection zone and gradually increased with distance from the disinfection zone. A safe buffer zone can be left if required between the nearest person and the position of zero intensity of the UVC radiation.

Turning first to disinfection zone 17, this zone covers rearmost unoccupied seats 27 between the occupied zone 26 and the area near lavatories 28 or in the lavatories. There are no stationary or moving persons in zone 17, as detected by sensors 3, 13 and standard video cameras 11. Furthermore, no moving persons are detected in occupied zone 26 and no moving or stationary persons are detected by sensors 3, 13 in lavatory area 28 or in lavatories 29 themselves. Therefore it is safe to disinfect this zone.

Turning now to disinfection zones 18, 19 and to an intermediate zone 30 where a person 31 is seen walking toward the front of the aircraft 20, disinfection is being carried out in zones 18, 19 but no disinfection is being carried out in intermediate zone 30. This is because sensors 3, 13 and standard video cameras 11 positioned over seats in these zones and positioned on bulkheads 10 have detected no seated or moving persons in zones 18, 19 or in adjacent lavatory and galley areas 28, 32 but have detected a moving person 31 in the intermediate zone 30.

For disinfection to be carried out in intermediate zone 30, however, further logic must be applied by the controller 33 to control the UVC lamps 4 in their UVC units 9. This is because there is a moving person 31 adjacent both zones 18 and 19. Applying the logic previously described, because there is a person immediately adjacent zones 18 and 19, caution should be observed and no disinfection should take place. However, according to the invention, predictive motion path UVC radiation control is applied by the controller 33 to the UVC lamps 4. According to this logic, disinfection may be carried out immediately adjacent one or more moving or stationary persons based upon decisions made as to the direction of movement of those persons and their speed of movement.

Thus, if the person is sensed to be moving away from a zone, such as a person 31 moving away from zone 19, then disinfection may either commence or be continued there. Indeed, as the person moves further away, the disinfection zone may be increased to take up the space vacated by the moving person. Here therefore, as shown in FIG. 3, disinfection zone 19 may be increased in size to the left as person 31 continues walking towards the front of the aircraft. Conversely, the size of disinfection zone 18 may be reduced as person 31 continues to encroach on the zone.

Movement of persons in the cabin or cockpit is detectable by at least two methods which may be used individually or in combination for enhanced accuracy and safety. Firstly, the infra-red or ultrasound sensors 3, 13 may be used by the timing of signals reflected from a person being monitored to detect distance of the person from the sensor or sensors. Speed and direction of movement of the person may be determined from these data. Sensors 13 in the cabin ceiling may be used specifically to monitor movement of persons in aisles 34 of the cabin.

Secondly, video image analysis of images created by the video cameras 11 and video cameras comprised in the sensors 3 may be used to detect persons in the field of view and any movement of those persons in the cabin or cockpit may be monitored by this method.

In both cases, information as to the presence and movement of persons will be used by the controller or controllers 33 to determine whether it is safe to carry out disinfection in any given zone in the cabin or cockpit.

Under normal circumstances, disinfection of the aircraft will only be carried out during maintenance when the aircraft is on the ground, parked and empty, as shown in FIG. 4. Safety for such disinfection may be ascertained using the sensors and controller of the system according to the invention or may simply be ascertained by crew or cleaners having inspected the aircraft and closed it for disinfection. In any case, it may be wise to employ the system of the invention, following an inspection, to be sure that no-one on the aircraft has been missed.

The system of the invention additionally offers the possibility of disinfecting parts of the aircraft in flight, if necessary. For example, if a passenger or crew member is taken ill on the flight and may have a contagious disease then, depending on the flight mode, it may be appropriate to carry out a partial disinfection of that part of the aircraft which has been occupied by the sick passenger. Disinfection of the air conditioning system may also be carried out by the system of the invention if UVC lamps are fitted thereto. If the aircraft is in the mid part of its flight, for example and it is not sensible to divert the flight immediately, then disinfection may be appropriate.

In these circumstances, disinfection according to one of the scenarios described above may be carried out to disinfect the area occupied by the sick passenger and the passenger moved to a safe part of the aircraft. Once the passenger has been disembarked, part or all of the aircraft may again be disinfected. The system of the invention can employ algorithms to determine which part of the aircraft it is safe or possible to disinfect, based on the type of illness suspected of the passenger, the amount of the flight travelled and still to travel and the position of the sick passenger and other passengers around him or her. If necessary, rows of seats around the sick passenger may be vacated to allow for extended disinfection. Disinfection in those seats can then take place automatically, according to the system of the invention.

Figure 5:
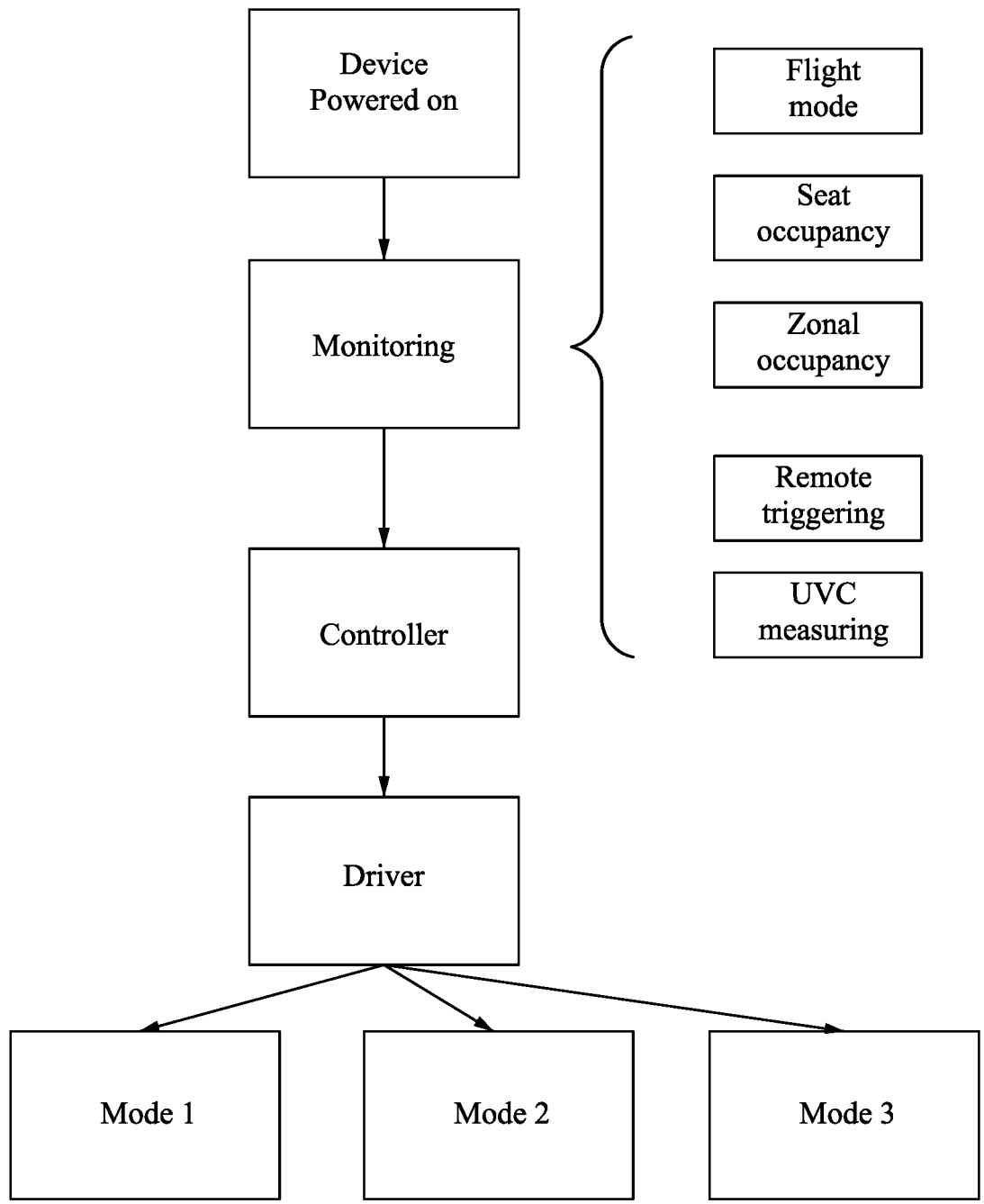
FIG. 5 is a flow chart of the method of operation of the invention.

FIG. 5 is a flow chart showing the broad operating principle of the system of the invention. It can be seen that, once the system has been powered on, monitoring of flight mode of the aircraft; seat occupancy; occupancy of zones (including movement of personnel); remote triggering of disinfection, and UVC measurement take place. In addition, temperatures of personnel may also be monitored.

All monitored parameters are then assessed by the one or more controllers which drive operation of the system to disinfect one or more zones or part zones of the aircraft cabin according to the flight mode of the aircraft. Mode 1 corresponds to activation of disinfection; Mode 2 corresponds to activation of visible light, and Mode 3 corresponds to activation of both UV and visible light.

The embodiments described herein are respective non-limiting examples of how the present technology, and aspects of the present technology, may be implemented. Any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined by the accompanying claims.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention is:

1. A cabin disinfection system for an aircraft, the system including:
a sensing device configured to sense presence and direction of movement of a person in one or more zones of an aircraft cabin to be disinfected,
one or more ultraviolet C (UVC) radiation sources adapted to disinfect the cabin in the one or more zones; and
a controller configured to control operation of the one or more UVC radiation sources by selecting one or more of the zones to apply UVC radiation to exposed surfaces in the selected one or more zones during the planned disinfection period, wherein the selection is dependent upon whether the sensing device senses the person in the one or more zones and whether the controller predicts, based on data received from the sensing device, that the person will occupy the one or more zones during the planned disinfection period of the selected one or more zones.

2. The cabin disinfection system according to claim 1, including a light intensity measuring device configured to measure intensity of UVC radiation emitted by the one or more UVC radiation sources in the selected one or more zones.

3. The cabin disinfection system according to claim 2, in which the controller is configured to adjust the light intensity of the one or more UVC radiation sources based on proximity of the person to the one or more UVC radiation sources.

4. The cabin disinfection system according to claim 1, wherein the controller is configured to count persons in the selected one or more zones.

5. The cabin disinfection system according to claim 1, wherein the controller is configured to count persons present in the cabin based on data received from the sensing device.

6. The cabin disinfection system according to claim 1, including one or more visible light sources controllable by the controller to illuminate the selected one or more zones.

7. The cabin disinfection system according to claim 6, in which the controller is configured to control the one or more visible light sources and the one or more UVC radiation sources to illuminate the selected one or more zones with at least one of: visible light, UVC radiation, a combination of visible light and UVC radiation, or no visible light and no UVC radiation.

8. The cabin disinfection system according to claim 1, in which the controller is configured to predict whether the person will occupy the selected one or more zones during the planned disinfection period based on data received from the sensing device indicating a current position and direction of movement of the person.

9. The cabin disinfection system according to claim 1, in which the controller is configured to predict whether the person will occupy the selected one or more zones during the planned disinfection period based on data received from the sensing device indicating the presence and the direction of movement of the person, and a speed of the movement of the person.

10. The cabin disinfection system according to claim 1, in which the sensing device is configured to sense the person in the selected one or more zones by detecting seat occupancy in seats in the selected one or more zones.

11. The cabin disinfection system according to claim 1, in which the sensing device includes a video camera operatively linked to video analytics software to sense the presence of persons.

12. The cabin disinfection system according to claim 11, in which the video camera includes an IR camera adapted to detect a body temperature of the person, and the controller is configured to issue an alert of a possible ill person based on the body temperature detected by the IR camera.

13. The cabin disinfection system according to claim 1, in which the controller is configured to control the one or more UVC radiation sources to apply a predetermined dose of UVC radiation to a selected region of the aircraft cabin.

14. The cabin disinfection system according to claim 1, in which the controller is configured to control the application of the UVC radiation depending on a flight mode of the aircraft.

15. The cabin disinfection system according to claim 1, including an array of multifunction UVC units distributed throughout the aircraft, wherein each of the multifunction UVC units includes at least one of the one or more UVC radiation sources and an UVC intensity sensing device, wherein at least two of the multifunction UVC units are operatively linked together.

16. The cabin disinfection system according to claim 15, wherein the sensing device includes an infra-red video camera.

17. The cabin disinfection system according to claim 16, wherein the infra-red video camera is activated by passive infra-red and ultrasonic movement sensors in at least one of the multifunction UVC units.

18. An aircraft including a cabin disinfection system according to claim 1.

19. The cabin disinfection system according to claim 1 wherein the controller is configured to prevent, during at least a portion of a planned disinfection period, application of UVC radiation from at least one of the one or more UVC radiation sources in a selected zone of the one or more of the zones if either the controller determines that the person is in the selected zone during the at least a portion of the planned disinfection period or the person is predicted to be in the zone during the at least a portion of the planned disinfection period.

\* \* \* \* \*